US008888995B2

(12) United States Patent
Hernandez et al.

(10) Patent No.: US 8,888,995 B2
(45) Date of Patent: Nov. 18, 2014

(54) METHOD FOR THE SUBLIMATION OR PYROLYSIS OF HYDROCARBONS USING RF ENERGY TO BREAK COVALENT BONDS

(75) Inventors: Victor Hernandez, Merritt Island, FL (US); Lisa Patton, Indialantic, FL (US)

(73) Assignee: Harris Corporation, Melbourne, FL (US)

( * ) Notice: Subject to any disclaimer, the term of this patent is extended or adjusted under 35 U.S.C. 154(b) by 655 days.

(21) Appl. No.: 13/209,102

(22) Filed: Aug. 12, 2011

(65) Prior Publication Data

US 2013/0041199 A1 Feb. 14, 2013

(51) Int. Cl.

| | |
|---|---|
| ***C07C 4/04*** | (2006.01) |
| ***C10G 15/08*** | (2006.01) |
| ***H05B 6/80*** | (2006.01) |
| ***C10B 19/00*** | (2006.01) |

(52) U.S. Cl.

CPC ................ *C10B 19/00* (2013.01); *C10G 15/08* (2013.01); *H05B 6/80* (2013.01); *H05B 2214/03* (2013.01)

USPC ................. 208/402; 204/157.15; 204/157.46; 204/205; 315/3.5; 315/3.6; 330/43; 333/120; 333/208

(58) Field of Classification Search

USPC ................... 422/186.29; 204/157.15, 157.63; 315/3.5, 3.6; 330/43

See application file for complete search history.

(56) References Cited

U.S. PATENT DOCUMENTS

| | | | | |
|---|---|---|---|---|
| 3,710,063 A | | 1/1973 | Aine | |
| 3,814,983 A | * | 6/1974 | Weissfloch et al. | 315/39 |
| 4,508,168 A | | 4/1985 | Heeren | 166/248 |
| 4,524,826 A | | 6/1985 | Savage | 166/248 |
| 4,714,810 A | | 12/1987 | Sirkis | |
| 4,817,711 A | | 4/1989 | Jeambey | 166/248 |
| 7,598,898 B1 | | 10/2009 | Funk et al. | |
| 2005/0103307 A1 | | 5/2005 | Yoshimoto | |
| 2006/0112639 A1 | | 6/2006 | Nick | |
| 2006/0251557 A1 | * | 11/2006 | Fanson et al. | 423/213.5 |
| 2007/0056880 A1 | * | 3/2007 | Moreira et al. | 208/189 |
| 2008/0265654 A1 | | 10/2008 | Kearl et al. | |
| 2008/0296294 A1 | | 12/2008 | Uhm | |
| 2010/0219108 A1 | | 9/2010 | Parsche | |

(Continued)

FOREIGN PATENT DOCUMENTS

| | | |
|---|---|---|
| DE | 102009046881 | 5/2011 |
| WO | 2004057175 | 7/2004 |

(Continued)

OTHER PUBLICATIONS

Tomiyasu, K. (1960). IRE Transactions on Microwave Theory and Techniques, 8(2), 253-254.*

(Continued)

*Primary Examiner* — Brian McCaig

(74) *Attorney, Agent, or Firm* — Allen, Dyer, Doppelt & Milbrath & Gilchrist, P.A.

(57) ABSTRACT

High power RF energy supplied to a reaction chamber at a resonant frequency is used to break the covalent bonds of a hydrocarbon material without heat. An RF signal generator may be used to supply RF energy to a resonant ring through a four port coupler. The phase of the RF energy passing through the resonant ring may be adjusted to achieve an integral multiple of a resonant wavelength. Wavelength and intensity may be adjusted to sublimate or pyrolyze the hydrocarbon material to yield a useful gaseous product.

22 Claims, 5 Drawing Sheets

(56) References Cited

U.S. PATENT DOCUMENTS

| | | | |
|---|---|---|---|
| 2011/0277474 | A1 | 11/2011 | Constantz et al. |
| 2012/0321526 | A1 | 12/2012 | Hernandez et al. |
| 2013/0120077 | A1 | 5/2013 | Hernandez et al. |

FOREIGN PATENT DOCUMENTS

| | | |
|---|---|---|
| WO | 2006083829 | 8/2006 |
| WO | 2008115226 | 9/2008 |
| WO | 2012173918 | 12/2012 |

OTHER PUBLICATIONS

John F. Gerlin, "Waveguide components and configurations for optimal performance in microwave heating systems", source: http://www.rfdh.com/ez/system/db/lib_app/upload/1774/%5BGerling%5D_Waveguide_Components_and_Configurations_for_Optimal_Performance_in_Microwave, 2000, pp. 1-8.

El harfi et al., "Pyrolysis of the Moroccan (Tarfaya) Oil Shales Under Microwave Irradiation", 2000, vol. 79, pp. 733-742.

Bao et al., Study on Main Factors Influencing Actylene Formation During Coal Pyrolysis in Arc Plasma', 2006, vol. 84, pp. 222-226.

Thomsen et al., Pressurized Laser Pyrolysis of Coal', 1995, vol. 34, pp. 243-250.

Gasner et al., "Microwave and Conventional Pyrolysis of a Bituminous Coal", 1986, pp. 1-8.

Bodily et al., "Microwave Pyrolysis of Coal and Related Hydrocarbons", 1976, pp. 221-226.

Veshcherevich, "Resonant Ring for High Power Tests of RF Couuplers", Cornell University: ERL Reports—2003, ERL Mar. 15, pp. 1-20.

Tomiyasu, "Attenuation in a Resonant Ring Circuit", IRE Transactions on Microwave Theory and Techniques, vol. 8, Issue 2, 1960, pp. 253-254.

* cited by examiner

METHOD FOR THE SUBLIMATION OR PYROLYSIS OF HYDROCARBONS USING RF ENERGY TO BREAK COVALENT BONDS

CROSS REFERENCE TO RELATED APPLICATIONS

This application is related to U.S. Pat. No. 8,674,785 issued Mar. 18, 2014 and U.S. Patent Publication No. 2012-0321526 published Dec. 20, 2012, both of which are hereby incorporated herein in their entirety.

BACKGROUND OF THE INVENTION

The present invention relates to the sublimation and pyrolysis of hydrocarbons. In particular, the present invention relates to the sublimation and pyrolysis of hydrocarbons using radio frequency (RF) energy amplified by a ring resonator.

As the world's standard crude oil reserves are depleted, and the continued demand for oil causes oil prices to rise, attempts have been made to process all manner of hydrocarbons in increasingly varied ways. For example, attempts have been made to heat subsurface heavy oil bearing formations using steam, microwave energy and RF energy. However, these attempts have been generally inefficient and costly.

Sublimation or pyrolysis of substances such as coal and shale oil may yield valuable products, such as natural gas. Sublimation is essentially taking a material from its solid phase to its gaseous phase without the presence of a liquid phase. Pyrolysis, on the other hand, involves the chemical decomposition of organic substances by heating to break down hydrogen bonds. Such a process may produce natural gas from the sublimated or pyrolyzed substances with low greenhouse gas emissions. However, existing technologies require more energy to sublimate or pyrolyze substances such as coal or shale oil than the energy that is produced.

Pyrolysis differs from other processes (combustion and hydrolysis) in which the reactions do not involve oxygen or water. Pyrolysis of organic substances typically produces gas and liquid products and leave behind a carbon rich solid residue. In many industrial applications, the process is done under pressure and at operating temperatures above 430° C. Since pyrolysis is endothermic, problems with current technologies exist in which biomass substances are not receiving enough heat to efficiently pyrolyze and result in poor quality. For such cases, it becomes imperative for an initiation reaction to be used to enhance the amount of heat applied to the hydrocarbon material.

As the organic chemical structures of various hydrocarbons ages, the aromaticity (defined as the ratio of aromatic carbon to total carbon) increases. These aromatic structures are chains of carbons that are targeted for breaking during heating processes. In order for the production of natural gas to occur, these large complex structures break during reactions and thus, increase the solubility of the organic portion of the substance. Some of these reactions are (but not limited to) cracking, alkylation, hydrogenation, and depolymerization.

Thus, various hydrocarbon materials must be extensively processed in order to achieve maximum fuel production. In industry, upgrading facilities are used in order to further make the material usable and more valuable. It is possible that the RF energy applied in this technology could be used to also change the molecular structure of the material by breaking it into smaller components bypassing the need for the hydrocarbons to be processed and treated at upgrading facilities.

It is known that a resonant ring may be used to generate a very large electromagnetic field and to couple this RF power through a coupling mechanism to a reaction chamber. In order to achieve the high field amplitude required, the resonant mechanism referred hereafter as the ring most be in a state of resonance at its operating frequency. To effect this, the length of the ring has to be an integral number of guide wavelengths of the coupled wave. The waves coupled through the resonant ring, along with the directional coupler, create an effective power gain. The amplitude of this wave front can be tracked and measured throughout this process by appropriately incrementing the resonant ring. To build a resonant ring, two couplers of similar design are implemented with a coupling structure between them. The coupling structure can be of either waveguide or coaxial transmission line. The cavity provides the needed bandwidth to track the dependence of the cavity frequency to the dimension of the ring.

SUMMARY OF THE INVENTION

In one embodiment, a method for processing hydrocarbons comprises containing a hydrocarbon material in a reaction chamber connected to a resonant ring, transmitting radio frequency energy to the resonant ring through a four-port coupler, amplifying the radio frequency energy using the resonant ring, and receiving the radio frequency energy in the reaction chamber to process the hydrocarbon material by breaking covalent bonds of the hydrocarbon material.

The method may further comprise monitoring the power level in the resonant ring. Dielectric pressure ports may be used to connect the reaction chamber to the resonant ring. The method may further comprise monitoring the content of a gas stream leaving a gas port on the reaction chamber. This monitoring may be accomplished using a gas chromatograph to monitor the gas stream leaving the gas port of the reaction chamber. The method may further comprise monitoring the pressure and temperature in the resonant cavity of the reaction chamber.

In another embodiment, a method for processing hydrocarbons comprises connecting a radio frequency signal generator to a four-port coupler at a first port on the four-port coupler, connecting a second port and a third port on the four-port coupler to a resonant ring, the resonant ring including a phase adjuster and a reaction chamber, the reaction chamber having a resonant cavity, connecting a dummy load to the four-port coupler at a fourth port, placing hydrocarbons in the reaction chamber, operating the radio frequency signal generator to generate radio frequency energy; directing at least a portion of the radio frequency energy to a resonant ring at a third port of a four-port coupler and through the reaction chamber and the phase adjuster to the second port, and adjusting the phase of the electrical current by operating the phase adjuster to achieve an integral multiple of a resonant wavelength such that radio frequency energy in the reaction chamber breaks the covalent bonds between molecules of hydrocarbons in the reaction chamber.

The method may further comprise connecting a power meter to the resonant ring; connecting a pressure measurement device and a temperature measurement device to the reaction chamber to measure pressure and temperature within the resonant cavity; connecting dielectric pressure ports between the reaction chamber and the resonant ring; connecting a gas port to the reaction chamber; and/or monitoring a gas stream leaving the gas port of the reaction chamber. A gas chromatograph may be used to monitor the gas stream leaving the gas port of the reaction chamber.

In yet another embodiment, a method for processing hydrocarbons comprises operating a radio frequency signal generator connected to a first port of a four-port coupler to generate radio frequency energy, wherein at least a portion of the radio frequency energy is directed to a resonant ring at a third port of the four-port coupler and through a reaction chamber and a phase adjuster in the resonant ring to a second port of the four-port coupler; and adjusting the phase of the electrical current using the phase adjuster to achieve an integral multiple of a resonant wavelength such that radio frequency energy in the reaction chamber breaks the covalent bonds between molecules of the hydrocarbons in reaction chamber.

In this embodiment, a portion of the radio frequency energy may flow to a dummy load connected to a fourth port of the four-port coupler. The method may further comprise: monitoring the power level in the resonant ring; monitoring the pressure and temperature in the resonant cavity of the reaction chamber; and monitoring the content of a gas stream leaving a gas port on the reaction chamber. A gas chromatograph may be used to monitor the gas stream leaving the gas port of the reaction chamber. In addition, dielectric pressure ports may be used to connect the reaction chamber to the resonant ring.

Other aspects of the invention will be apparent from this disclosure.

DETAILED DESCRIPTION OF THE PREFERRED EMBODIMENTS

The subject matter of this disclosure will now be described more fully, and one or more embodiments of the invention are shown. This invention may, however, be embodied in many different forms and should not be construed as limited to the embodiments set forth herein. Rather, these embodiments are examples of the invention, which has the full scope indicated by the language of the claims.

Figure 1:
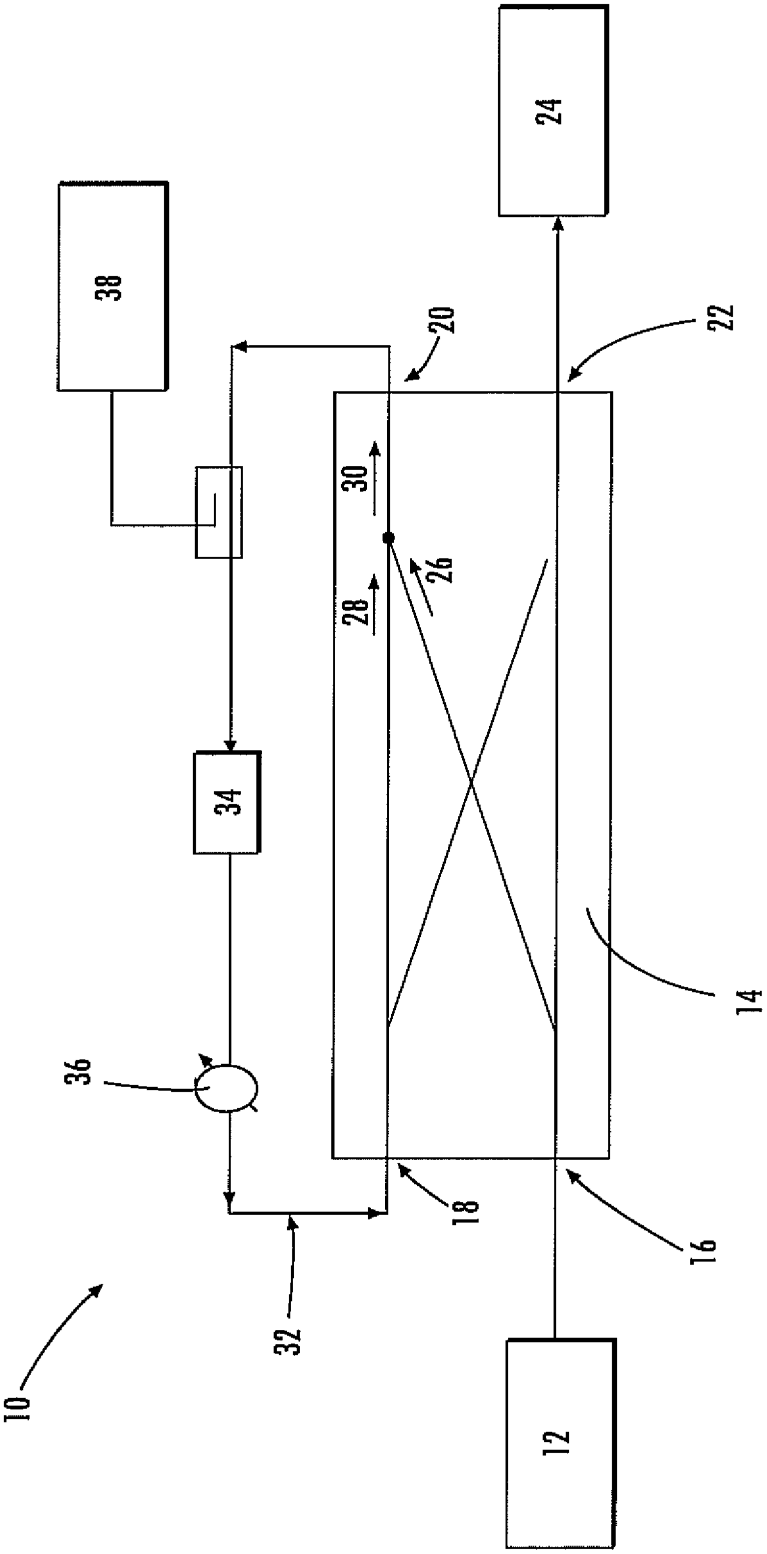
FIG. 1 illustrates an embodiment of the present process for sublimation/pyrolysis using RF energy.

FIG. 1 illustrates an embodiment of the present apparatus 10 for sublimation/pyrolysis of coal, shale oil and other hydrocarbons using RF energy. An RF signal generator 12 supplies power to a resonant ring 32 through a four-port coupler 14. For the purpose of this invention, a transmitter of a non-specific power range is used to supply power to the resonant ring. RF signal generator 12 is connected to four-port coupler 14 at first port 16. Electrical power 26 generated by RF signal generator 12 enters resonant ring 32 at third port 20 and travels through reaction chamber 34 and phase adjuster 36, and returns to four port coupler 14 at second port 18. All or a portion of this power joins incoming power 26 from RF signal generator 12 to form power 30, which then repeats the circuit around resonant ring 32. A power meter 38 may be connected to resonant ring 32 between third port 20 and reaction chamber 34.

The resonant cavity may be used to contain hydrocarbon material and provide a flexible pyrolysis/sublimation reaction chamber for evaluating optimal RF frequency versus RF power versus secondary bias source (wavelength and intensity) for a given heat range. RF discharge plasma generated in the resonant cavity 52 of the reaction chamber 34 (see FIG. 2) creates a measurable gas production. The resonant ring 32 will support continuous fuel production and can be tuned as discussed below.

The structure of resonant ring 32 and phase adjuster 36 serve to "tune" resonant ring 32 to a resonant frequency of reaction chamber 34 to optimize sublimation/pyrolysis in reaction chamber 34. Phase adjuster 36 can adjust the phase of the wave front 30 traveling resonant ring 32 to achieve an integral multiple of the resonant wavelength. The RF energy in reaction chamber 34 is used to break the covalent bonds of hydrocarbon molecules placed in reaction chamber 34 without heat. As a result, temperatures in reaction chamber may be optimal for sublimation and/or pyrolysis. Sublimation will convert the material, whereas the pyrolysis will decompose it by breaking its covalent bonds. During the pyrolysis decomposition process, the heavy material will break down into lighter more desirable compounds. This will be achieved by synchronizing the RF signal field of generator 12 with the resonant ring 32 propagation characteristics. Tuning the process within its operating temperature range, approximately 45° C.-500° C., may be useful to favor the decomposition process discussed (break the covalent bonds). In addition this process promotes the generation of hydrogen and minimize the production of sulfur. This is a form of upgrading which the sublimation and/or pyrolysis process brings about and results in the production of natural gas. The tuning of the power to reach the desired temperature for this process to occur provides an optimally lower temperature and minimizes energy consumption, which improves system efficiency.

A dummy load 24 is a passive device connected to four-port coupler 14 at fourth port 22. Dummy load 24 is used to absorb and dissipate energy not needed for the sublimation/pyrolysis process. Thus, not all power entering four port coupler 14 at second port 18 joins the power 26 from signal generator 12 as some may be diverted to dummy load 24. The four port coupler is sized appropriately to minimize the dissipated power to insure system efficiency.

Figure 2:
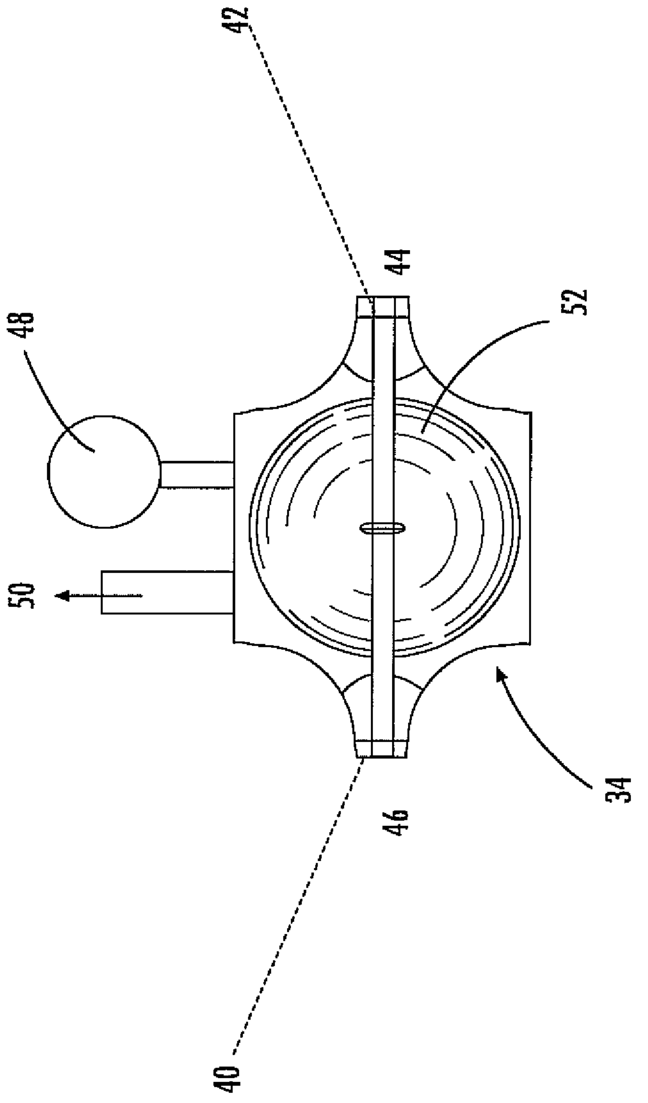
FIG. 2 illustrates a reaction chamber associated with the present process for sublimation/pyrolysis using RF energy of FIG. 1.

FIG. 2 provides a closer look at reaction chamber 34, which is shown separate from resonant ring 32. RF energy enters reaction chamber 34 at first connection 44 and exits at second connection 46. Reaction chamber 34 is coupled to resonant ring 32 through dielectric pressure ports 40 and 42. Dielectric pressure ports 40 and 42 are windows that are transparent to RF energy, but mechanically isolate resonant cavity 52 of reaction chamber 34 from the resonant ring 32 with regard to the material sublimation/pyrolysis process taking placed in reaction chamber 34. The construction of the reaction chamber is not materials specific and may consist of one or combination of suitable materials.

RF energy is used to break the covalent bonds of hydrocarbons introduced into resonant cavity 52 of reaction chamber 34 and release gaseous products, which then exit reaction chamber 34 at gas port 50. A gas chromatograph (not shown) may be connected in the gas stream at or near gas port 50 to monitor the byproducts of the content of the gas stream leaving reaction chamber 34 to facilitate tuning of the process. This gas stream 34 may contain lighter components, such as, but not limited to methane, propane, and various derivatives of alcohols. Such off-gasing components will exist during the process (both sublimation and pyrolysis) temperatures are in the range of 45° C.-500° C. Pressure and temperature measurement devices 48 are in functional contact with resonant cavity 52.

Equating component waves around resonant ring 32 may be predicted according to the following formulas:

$$E_4 = E_4 e^{-i\phi}\left(10^{\frac{-\partial}{20}}\right)\sqrt{1-c^2} + cE_1$$

$$cE_1 = E_4\left(1 - e^{-i\phi}\left(10^{\frac{-\partial}{20}}\right)\sqrt{1-c^2}\right)$$

$$\frac{E_4}{E_1} = \frac{c}{1 - e^{-i\phi}\left(10^{\frac{-\partial}{20}}\right)\sqrt{1-c^2}}$$

$$\frac{P_4}{P_1} = \left\{\frac{c}{1 - e^{-i\phi}\left(10^{\frac{-\partial}{20}}\right)\sqrt{1-c^2}}\right\}^2$$

$$G_{linear} = \left\{\frac{c}{1 - \left(10^{\frac{-\partial}{20}}\right)\sqrt{1-c^2}}\right\}^2$$

$$G_{linear} = \left\{\frac{10^{\frac{-C}{20}}}{1 - \left(10^{\frac{-\partial}{20}}\right)\sqrt{1-\left(10^{\frac{-C}{20}}\right)^2}}\right\}^2$$

Where:

Glinear=the linear power gain;

α=the attenuation around the loop in dB;

Φ=2πnλ, where n is an integer;

C=coupling factor in dB; and c=10−C/20

The ring performance can be measured using the power gain equation which is dependent on several variables within the system: coupling coefficient, attenuation and reflection in the ring, transmission, and electrical length.

Figure 3:
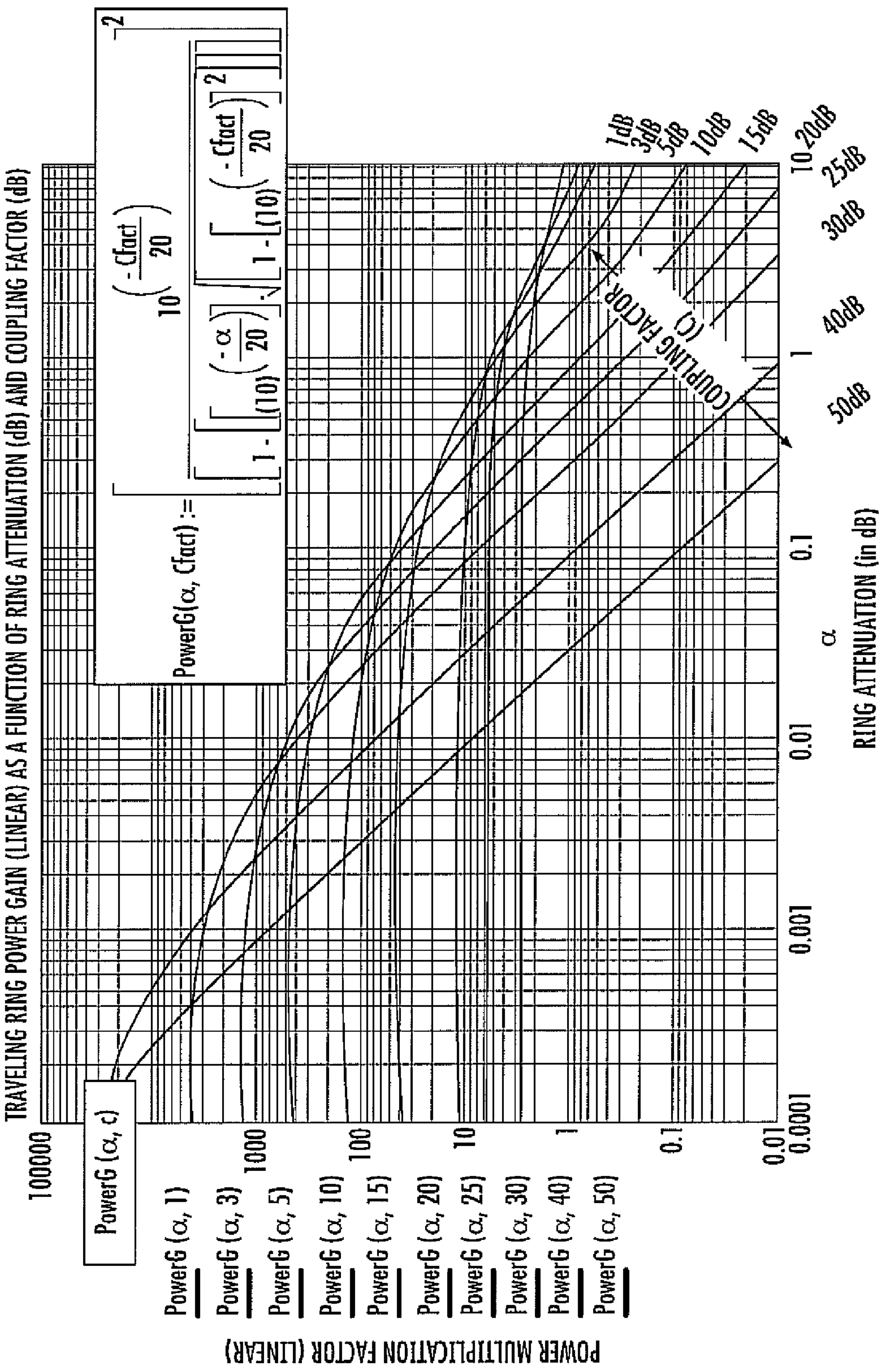
FIG. 3 illustrates the ring power gain as a function of ring attenuation for the embodiment illustrated in FIG. 1.
Figure 4:
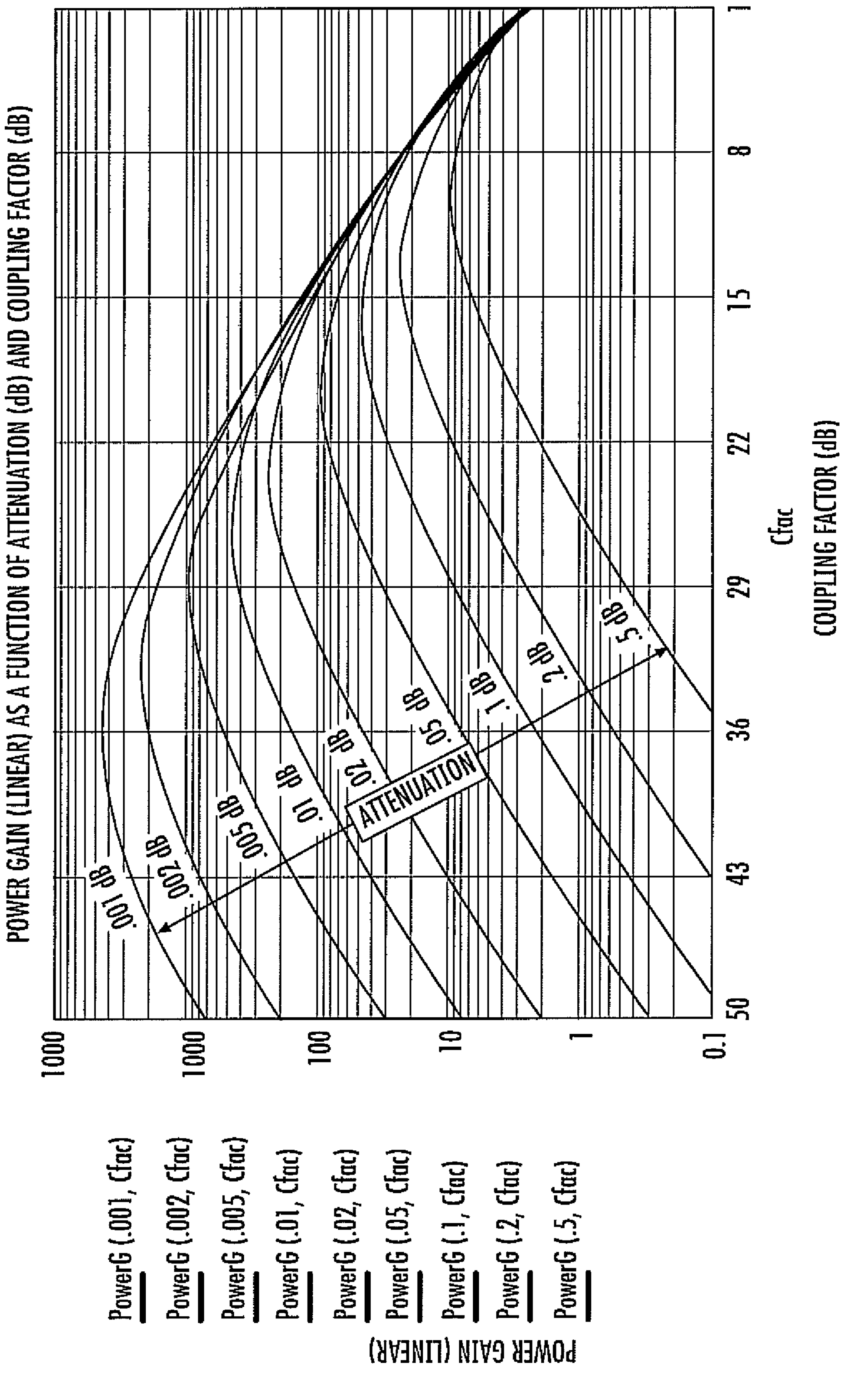
FIG. 4 illustrates the ring power gain as a function of coupling factor for the embodiment illustrated in FIG. 1.
Figure 5:
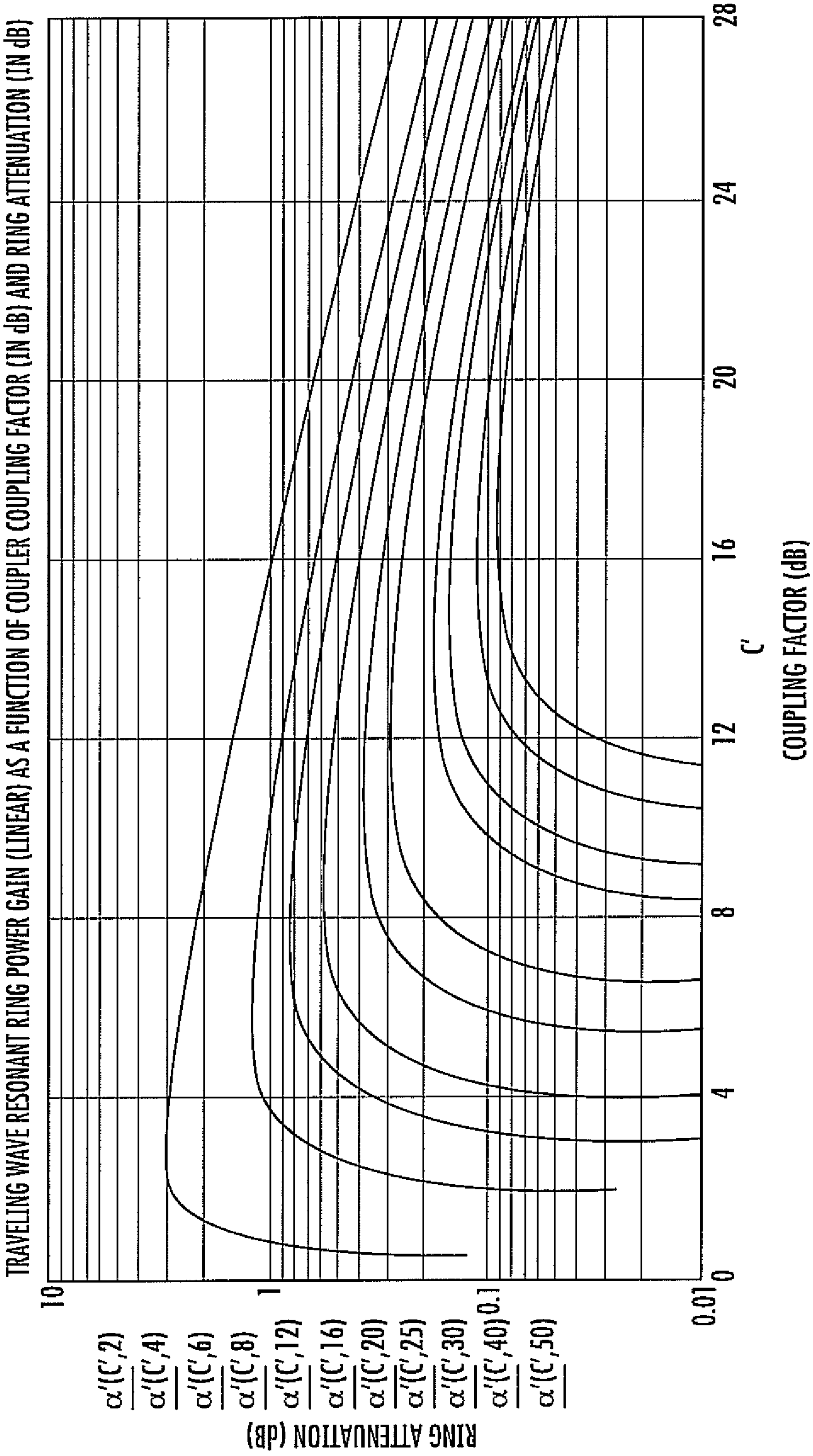
FIG. 5 illustrates the ring attenuation as a function of coupling factor for the embodiment illustrated in FIG. 1.

FIGS. 3-5 illustrate performance characteristics of resonant ring 32 in three different ways. Turning to FIG. 3, the power gain (G) of resonant ring 32 is shown as a function of ring attenuation (a). Coupling factor (C) is represented across the graph, as four port coupler 14 is variable in character. The present apparatus for sublimation/pyrolysis using RF energy 10 is designed to have a very small power loss around resonant ring 32.

FIG. 4 looks at the performance of resonant ring 32 using the power gain (G) around resonant ring 32 as a function of coupling factor (C). Here, ring attenuation (α) is represented across the graph. There exists the optimal coupling coefficient and the power gain is maximal.

In FIG. 5, the ring attenuation (α) is shown as a function of coupling factor (C). Power gain (G) is represented across the graph at the high end of the coupling factor (C). This figure is another way to express the traveling wave guide and determine the maximum power gain possible at the specified coupling factor.

Overall, a signal generator is coupled to a resonant ring test fixture. The resonant cavity is structured in such a way to receive high power and synchronize the RF signal generator with the resonant ring structure. The pyrolysis and/or sublimation reaction chamber is coupled to the resonant ring through dielectric ports. This reaction chamber is designed to easily evaluate the optimal RF frequency, RF power, and wavelength and intensity in order to maximize the amount of outputs from the hydrocarbon substance that is under test. RF discharge substances generated during the chemical reactions of the pyrolysis/sublimation are to be measured and analyzed. The resonant ring is designed to support continuous operation.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged either in whole or in part. Therefore, the spirit and scope of the appended claims should not be limited to the description of the preferred versions contained herein.

The invention claimed is:

1. A method for processing hydrocarbons, the method comprising:
- containing a hydrocarbon material in a reaction chamber connected to a resonant ring;
- directing radio frequency energy to the resonant ring through a four-port coupler;
- amplifying the radio frequency energy using the resonant ring; and
- receiving the radio frequency energy in the reaction chamber to process the hydrocarbon material by breaking covalent bonds of the hydrocarbon material without use of a catalyst and without a microwave absorbent additive material.

2. The method of claim 1, further comprising generating the radio frequency energy using a radio frequency signal generator.

3. The method of claim 1, further comprising operating a phase adjuster in the resonant ring to achieve an integral multiple of a resonant wavelength of the radio frequency energy.

4. The method of claim 1, further comprising absorbing and dissipating a portion of the radio frequency energy using a dummy load connected to the four-port coupler.

5. The method of claim 1, further comprising monitoring the power level in the resonant ring.

6. The method of claim 1, wherein the step of receiving the radio frequency energy in the reaction chamber further comprises receiving radio frequency energy through a dielectric pressure port.

7. The method of claim 1, further comprising monitoring the content of a gas stream leaving a gas port on the reaction chamber.

8. The method of claim 1, further comprising monitoring the pressure and temperature in the reaction chamber.

9. A method for processing hydrocarbons, the method comprising:
- connecting a radio frequency signal generator to a four-port coupler at a first port on the four-port coupler;
- connecting a second port and a third port on the four-port coupler to a resonant ring, the resonant ring including a phase adjuster and a reaction chamber, the reaction chamber having a resonant cavity;
- connecting a dummy load to the four-port coupler at a fourth port;
- placing hydrocarbons in the reaction chamber;
- operating the radio frequency signal generator to generate radio frequency energy;

directing at least a portion of the radio frequency energy to a resonant ring at a third port of a four-port coupler and through the reaction chamber and the phase adjuster to the second port; and adjusting the phase of the electrical current by operating the phase adjuster to achieve an integral multiple of a resonant wavelength such that radio frequency energy in the reaction chamber breaks the covalent bonds between molecules of hydrocarbons in the reaction chamber without use of a catalyst and without a microwave absorbent additive material.

10. The method of claim 9, further comprising the step of connecting a power meter to the resonant ring.

11. The method of claim 9, further comprising the step of connecting dielectric pressure ports between the reaction chamber and the resonant ring.

12. The method of claim 9, further comprising the step of connecting a gas port to the reaction chamber.

13. The method of claim 12, further comprising the step of monitoring a gas stream leaving the gas port of the reaction chamber.

14. The method of claim 13, wherein the step of monitoring a gas stream further comprises connecting a gas chromatograph to the gas port of the reaction chamber.

15. The method of claim 9, further comprising the step of connecting a pressure measurement device and a temperature measurement device to the reaction chamber to measure pressure and temperature within the resonant cavity.

16. A method for processing hydrocarbons, the method comprising:

operating a radio frequency signal generator connected to a first port of a four-port coupler to generate radio frequency energy, wherein at least a portion of the radio frequency energy is directed to a resonant ring at a third port of the four-port coupler and through a reaction chamber and a phase adjuster in the resonant ring to a second port of the four-port coupler; and adjusting the phase of the electrical current using the phase adjuster to achieve an integral multiple of a resonant wavelength such that radio frequency energy in the reaction chamber breaks the covalent bonds between molecules of the hydrocarbons in reaction chamber without use of a catalyst and without a microwave absorbent additive material.

17. The method of claim 16, further comprising directing a portion of the radio frequency energy from the second port to a dummy load connected to a fourth port of the four-port coupler.

18. The method of claim 16, further comprising monitoring the power level in the resonant ring.

19. The method of claim 16, further comprising receiving radio frequency energy in the reaction chamber through a dielectric pressure port.

20. The method of claim 16, further comprising monitoring the content of a gas stream leaving a gas port on the reaction chamber.

21. The method of claim 20, wherein the step of monitoring the content of a gas stream leaving a gas port on the reaction chamber further comprises connecting a gas chromatograph to the gas port of the reaction chamber.

22. The method of claim 16, further comprising monitoring the pressure and temperature in the reaction chamber.

* * * * *